US010551385B2

(12) United States Patent
Skog et al.

(10) Patent No.: US 10,551,385 B2
(45) Date of Patent: Feb. 4, 2020

(54) PREDICTING CANCER PROGRESSION

(71) Applicant: AROCELL AB, Uppsala (SE)

(72) Inventors: Sven Skog, Huddinge (SE); Staffan Eriksson, Lidingö (SE); Bernard Tribukait, Drottingholm (SE); Qimin He, Huddinge (SE)

(73) Assignee: AROCELL AB, Uppsala (SE)

( * ) Notice: Subject to any disclaimer, the term of this patent is extended or adjusted under 35 U.S.C. 154(b) by 0 days.

(21) Appl. No.: 15/357,762

(22) Filed: Nov. 21, 2016

(65) Prior Publication Data

US 2017/0067900 A1    Mar. 9, 2017

Related U.S. Application Data

(60) Continuation of application No. 12/626,802, filed on Nov. 27, 2009, now abandoned, which is a division of application No. 10/555,935, filed as application No. PCT/SE2004/000750 on May 14, 2004, now abandoned.

(60) Provisional application No. 60/471,245, filed on May 16, 2003.

(51) Int. Cl.
*G01N 33/574* (2006.01)

(52) U.S. Cl.
CPC ............ *G01N 33/57488* (2013.01); *G01N 2333/91215* (2013.01); *G01N 2800/54* (2013.01)

(58) Field of Classification Search
None
See application file for complete search history.

(56) References Cited

U.S. PATENT DOCUMENTS

| 5,698,409 A | 12/1997 | O'Neill |
| 6,083,707 A | 7/2000 | Eriksson et al. |
| 2001/0023419 A1* | 9/2001 | Lapointe ............... G16H 50/20 706/15 |

FOREIGN PATENT DOCUMENTS

| WO | 95/04758 A1 | 2/1995 |
| WO | 2004/013630 A1 | 2/2004 |

OTHER PUBLICATIONS

Gohji, K. et al., "Prognostic Significance of Circulating Matrix MetaUoproteinase-2 to Tissue Inhibitor of MetaUoproteinases-2 Ratio in Recurrence of Urothelial Cancer after Complete Resection", Cancer Research 56, J, pp. 3196-3198 (Jul. 1996).
Tini et al., Generation and application of chicken egg-yolk antibodies, Comparative Biochemistry and Physiology, Part A: Molecular & Integrative Physiology, 131(3):569-74 (Mar. 2002).
Robertson et al., Thymidine Kinase in Breast Cancer, British Journal of Cancer, 62:663-667 (Oct. 1990).
O'Neill et al., Can Thymidine Kinase Levels in Breast Tumors Predict Disease Recurrence?, J Natl Cancer Inst., 84(23):1825-1828 (Dec. 2, 1992).
He et al., "Existence of phosphorylated and dephosphorylated forms of cytosolic thymidine kinase (TKI)", Biochimica et Biophysica Acta, 1289:25-30 (1996).
Wang et al., "Investigation on cell proliferation with a new antibody against thymidine kinase 1 Analytical Cellular Pathology", 23:11-19 (2001).
Kuroiwa et al., "Specific recognition of cytosolic thymidine kinase in the human lung tumor by monoclonal antibodies raised against recombinant human thymidine kinase", Journal of Immunological Methods, 253 (2001).
Voller et al., "Development of human anti-thymidine kinase antibodies", Anti-Cancer Drugs, vol. 12:555-559 (2001).
Gronowitz et al., "The use of serum deoxythymidine kinase as a prognostic marker, and in the monitoring of patients with non-Hodgkin's lymphoma", Br. J. Cancer, 47:487-495 (1983).
Karstrom et al., "Molecular forms in human serum of enzymes synthesizing DNA precursors and DNA", Molecular and Cellular Biochemistry, 92:23-35 (1990).
Ke et al., "Mitotic Degradation of Human Thymidine Kinase 1 Is Dependent on the Anaphase-Promoting ComplexICyc losome-Cdhl-Mediated Pathway", Molecular and Cellular Biolog, 24(2), pp. 514-526 (Jan. 2004).
Scholzen et al., "The Ki-67 Protein: From the Known and the Unknown", Journal of Cellular Physiology, 182:311-322 (2000).
Wintersberger, "DNA Damage and Mutagenesis", Biochemical Society Transactions, vol. 25:1-6 (Jul. 19, 1996).
Wilson, "Assessment of Human Tumour Proliferation Using Bromodeoxyuridine-Current Status", Acta Oncologica, vol. 30, 8:903-910 (1991).
Tribukait, "Flow cytometry in assessing the clinical aggressiveness of genito-urinary neoplasms", World J. Urol., 5:108-122 (1987).
Foekens et al., "Thymidine Kinase and Thymidylate Synthase in Advanced Breast Cancer: Response to Tamoxifen and Chemotherapy", Cancer Research, 61:1421-1425 (Feb. 15, 2001).
Brae et al., "Thymidine Kinase as a Proliferative Marker: Clinical Relevance in 1.692 Primary Breast Cancer Patients", Journal oj Clinical OncoloHY, vol. 19, 11:2778-2787 (Jun. 2, 2001).

(Continued)

*Primary Examiner* — Brad Duffy
(74) *Attorney, Agent, or Firm* — Porter Wright Morris & Arthur LLP

(57) ABSTRACT

Method of determining a likelihood of cancer relapse in a subject who has completed cancer tumor surgery, radiotherapy treatment and/or chemotherapy treatment comprises contacting an antibody that binds specifically to a serum form of thymidine kinase 1 (STK1) protein with a blood serum sample one to six months after completing the surgery and/or treatment, and before any cancer relapse has been detected; determining an amount of antibody binding to STK1 protein in the sample; correlating the amount of antibody binding to STK1 protein to a concentration of STK1 protein in the sample; and based on the concentration of STK1 protein in the sample, generating decision support information representative of a likelihood of cancer relapse in the subject one to ten years after completion of the surgery and/or treatment, the decision support information comprising a likelihood value defining one of a high or low likelihood of cancer relapse.

5 Claims, 7 Drawing Sheets

Figure 1:
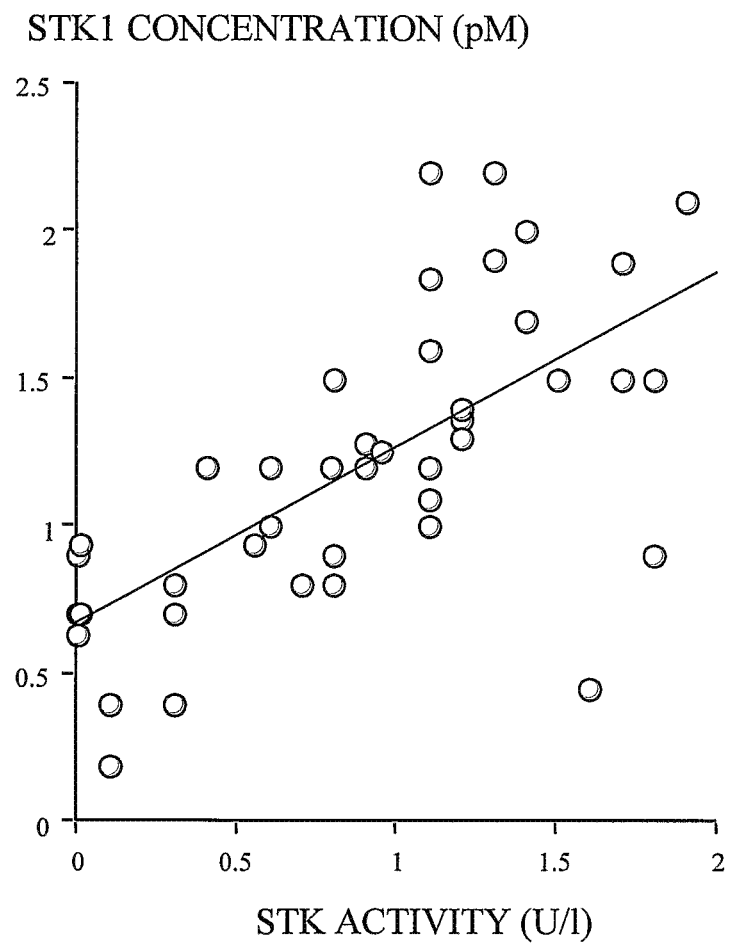

Specification includes a Sequence Listing.

(56) References Cited

OTHER PUBLICATIONS

Mao et al., "A Comparative Study: Immunohistochemical Detection of Cytosolic Thymidine Kinase and Proliferating Cell Nuclear Antigen in Breast Cancer" Cancer Investigation. vol. 20, 7 & 8:922-931(2002).

He et al., "Cell cycle related studies on thymidine kinase and its isoenzymes in Ehrlich ascites tumours", Cell Prolif., 24:13-14 (1991).

Hengtschlager et al., "Different Regulation of Thymidine Kinase during the Cell Cycle of Normal Versus DNA Tumor Virus-transformed Cells", The Journal of Biological Chemistry, vol. 269, 19:13836-13842 (May 13, 1994).

Munch-Petersen et al., "Diverging Substrate Specificity of Pure Human Thymidine Kinases 1 and 2 Against Antiviral Dideoxynucleosides", The Journal of Biological Chemistry, vol. 266, 14:9032-9038 (May 15, 1991).

Kauffman et al., "Cell Cycle Regulation of Thymidine Kinase: Residues Near the Carboxyl Terminus Are Essential for he SQecific Degradation of the Enzyme at Mitosis", Molecular and Cellular Biology, pp. 2538 2546 (May 1991).

Sherley et al., "Regulation of Human Thymidine Kinase during the Cell Cycle," The Journal of Biological Chemistry, vol. 263, 17:8350-8358 (Jun. 15, 1988).

Wu et al., "A New Cell Proliferating Marker: Cytosolic Thymidine Kinase as Compared to Proliferating Cell Nuclear Antigen in Patients with Colorectal Carcinoma", Anticancer Research, 20:4815-4820 (2000).

He et al, "The clinical significance of thymidine kinase I measurement in serum of breast cancer patients using anti-TKI antibody," The International Journal o/Biological Markers, vol. 15, 2:139-146 (2000).

Zou et al., "The half-life of thymidine kinase I in serum measured by ECL dot blot: a potential marker for monitoring the response to surgery of patients with gastric cancer", The International Journal 0/ Biological Markers. vol. 17, 2002. No. 2, pp. 135-140 (2002).

He et al., "Characterization of a peptide antibody against a C-terminal part of human and mouse cytosolic thymidinekinase, which is a marker for cell proliferation", European Journal o/Cell Biology, 70:117-124 (1996).

Nakao et al., "A Serial Determination of Serum Thymidine Kinase and Soluble Interleukin-2 Receptor Values Detects Early Phase Regrowth of Tumor Cells in Patients with Recurrent Malignant Lymphoma," Blood, 94:10, Suppl. part 2 Abstract (1999).

Gronowich et al., "Application of an in vitro assay for serum Thymidine Kinase: results on viral disease and malignancies in humans", Int. J. Cancer, 15:33 (1):5-12 (Jan. 1984).

Hall et al., "Immunohistochemical markers of cellular proliferation: achievements, problems and prospects", Cell Tissue Kinet., 23:505-522 (1990).

Wakao et al., "Serum Thymidine Kinase and Soluble Interleukin-2 Receptor Predict Recurrence of Malignant Lymphoma", pp. 140-146 (Feb. 9, 2002).

Mizutani et al., "Prognostic Significance of Thymidine Kinase Activity in Bladder Carcinoma", pp. 2120-2125 (Jun. 12, 2002).

Wintersberger, "DNA Damage and Mutagenesis", Biochemical Society Transactions, vol. 25, pp. 1-6 (Jun. 12, 2002).

Zhang et al., "Thymidine Kinase 1 Immunoassay: A Potential Marker for Breast Cancer", Cancer Detection and Prevention, 25(1 ):8-015 (2001).

Li et al., Clin. Cancer Res, Identification of Biomarkers for Breast Cancer in Nipple Aspiration and Ductal Lavage Fluid, 11(23):8312-8320 (Dec. 1, 2005).

Tsigris et al., Can. Letters, 184:215-222 (2002).

Database Gene seq [online] Jun. 6, 1996. retrieved from EBI Accession No. GSP:AAR84622. Database Accession No. AAR84662.

* cited by examiner

PREDICTING CANCER PROGRESSION

The Sequence Listing entitled "July-20-2018-Sequence-Listing ST25.txt" created Jul. 20, 2018, having a size of 3531 bytes, is incorporated herein by reference.

TECHNICAL FIELD

The present invention generally refers to monitoring and prediction of cancer diseases and in particular to early prediction of progression and recurrence of cancer diseases.

BACKGROUND

Cancer is a leading cause of death in human and the number of affected individuals increases for each year. Although the different methods of treatment for cancer, e.g. chemotherapy, endocrine therapy, radiotherapy and surgery, have improved tremendously the last decades, they are far from perfect, in particular for patients with late stages of cancer. Thus, much research has been spent on early detection of tumors in patients.

One used method for tumor and tumor stage detection is determination of cell proliferation in patients. The proportion of DNA-synthesizing cells (S-phase cells) in tumors has been used as a measure of their proliferation rate. The DNA-synthesizing cells have earlier been determined by means of radioactive-labeled thymidine (autoradiography). Incorporation of halogen-analogs of thymidine (BrdU) and antibodies against these have been used together with quantitative flow-cytometric DNA measurements. The disadvantage with the use of isotopic labeled thymidine and BrdU is that only living cells can be measured. Therefore, these methods have only been used on selected patients and in a limited number of studies [Wilson, *Acta Oncol,* 30; 903, 1991]. Furthermore, the flow-cytometry technique is unable to distinguish between proliferating and non-proliferating cells. Determination of S-phase cells is even more complicated in tumors, since the cancer tumor cells do not deviate in their DNA-content from benign cells [Tribukait, *World J. Urol,* 5: 108, 1987].

Instead of measuring DNA-synthesis itself, markers related to proliferating cells has been used, for example, Ki-67 and PCNA (Proliferating Cell Nuclear Antigen). Ki-67 is expressed in all cell cycle stages except for G0 [Scholzen, *J. Cellular Physiol,* 182: 311, 2000]. Antibodies against Ki-67 can be used on fresh tissues as well as on formaline feed and paraffin embedded tissues. Depending on the cell proliferation rate, PCNA is expressed in all cell cycle stages. PCNA is not as sensitive for various fixation techniques as Ki-67 [Hall, *Cell Tissue Kinet,* 25:502, 1990]. Antibodies against other types of proteins and enzymes involved in the DNA-synthesis (DNA polymerase, ribonucleotide reductase) have been tested, but with limited successful results [Wilson, *Acta Oncol.,* 30: 903, 1991].

Thymidine kinase (TK), an enzyme of the pyrimidine salvage pathway, catalyses the phosphorylation of thymidine to thymidine monophosphate. TK in human cells appears in two forms, a cytoplasmic (TK1) and a mitochondrial (TK2) protein, encoded by different genes. Human TK1 and TK2 are located on the chromosome 17q23.2-q25.3 and 16q22-q23.1, respectively. TK1 transcripts encode a 25.5 kDa protein with, highly conserved regions typical for nucleoside kinases. However, the crystal structures of this enzyme family have no yet been determined. The expression of TK1 is cell cycle regulated and the TK1 regulation is complex with mRNA levels peaking in proliferating cells. Splicing and translation of TK1 mRNA also varies in cells at different growth states, TK1 levels are mainly regulated by post-translational mechanisms, in particular by differential degradation due to highly active protease expression in mitotic cells. The C-terminal region of TK1 contains a specific sequence. KEN, which recently has been shown to be the signal for mitotic degradation of TK1 by the Anaphase-promoting complex/cyclosome-Cdh1-mediated pathway [Ke, *Mol. Cell. Biol.,* 24:514, 2004], TK2 is not cell cycle regulated and is the only TK enzyme found in resting cells [Wintersberger, *Biochem. Soc. Trans.,* 25:303, 1997; Sherley, *J. Biol. Chem.,* 263:8350, 1988; He, *Cell. Prolif.,* 24:3, 1991; Kauffman, *Mol. Cell. Biol.,* 11:2538, 1991; Hengstschläger, *J. Biol. Chem.,* 269:13836, 1994; Munch-Petersen, *J. Biol Chem.,* 266:9032, 1991].

The majority of the above-mentioned markers have been, used to identify proliferation cells in tissues. However, thymidine kinase activity has been determined in cytosol fractions of tissues as a proliferation marker in human breast cancer. In a study of 1,692 breast, cancer patient [Broet, *J. Clin. Oncol.,* 19:2778, 2000], high TK1 activity in the cytosol correlated to a shorter survival as well as a poor outcome of endocrine treatment (tamoxifen) [Foekens, *Cancer Res.,* 61:1421, 2001]. Furthermore, thymidine kinase has also been used as a marker of cell proliferation in serum by measuring its enzyme activity.

Because of the tight, coupling between the serum TK (STK) enzyme activity and high proliferation, it is considered a sensitive and useful marker for cell proliferation and hence for malignancy detection [He, *Internal J. Biol Marker,* 15:139, 2000; Zou, *Internal. J. Biol Marker,* 17:135, 2002; He, *Biochimica Biophysica Acta,* 1289:25, 1996; He, *Europ. J. Cell Biol.,* 70:117, 1996; Wu, *Anticancer Res.,* 6:4867, 2000; Mao, *Cancer Inves.* 20:922, 2002; Wang, *Analysis Cell. Pathology,* 23:11, 2001; Kuroiwa, *J. Immuno. Methods,* 253; 1, 2001], Thus, STK enzyme activity has been, used as a turner marker in patients with different blood tumors. However, STK activity has been found to be not a good marker in patients with solid tumors.

More than 95% of STK enzyme activity corresponds to TK1 while less than 5% corresponds to TK2. The composition and the properties of STK are not yet well understood. Results indicate that STK is a polymeric form of TK1, probably as complex also with other serum proteins and it has a total molecular weight of approximately 700 kDa [Karlström, *Mol. Cell. Biochem,* 92:23, 1990].

Using the thymidine analogue 5-iodo-2'-deoxyuridine as substrate, STK activity was established as a serological proliferation marker in 1984[Gronowich, *Br. J. Cancer,* 47:487, 1983] and is now available as a commercial RIA-kit-[$^{125}$I]-radio-assay (Sangtec Medical AB, Stockholm, Sweden, recently purchased by DiaSorin Inc.). The STK activity assay has been useful for estimation of tumor spread and prognosis in patients with the acute leukemia and chronic leukemia (CLL), Hodgkin and non-Hodgkin's lymphoma, but not in the case of solid tumors [Gronowich, *Int. J. Cancer,* 15:5, 1984]. The STK enzyme activity in CLL patient provides useful prognostic information regarding both responses to therapy and length of survival. Although the method is relatively effective, especially for leukemia and lymphoma diseases, the 5-iodo-2'-deoxyuridine is not a specific substrate for STK (TK1) activity. Furthermore, the [$^{125}$I]-radio-iodo-deoxyuridine has a short half-life (four weeks), the STK engine activity is highly sensitive to temperature and pH changes, and the radioassay requires specialized equipment (γ-scintillation counter), isotope laboratory and highly skilled, personnel. The disadvantages of such a radioassay technique have probably limited the clinical use of this assay.

Therefore, & new STK activity kit based on antibodies against the product of the STK reaction has recently been developed. Anti-TK1 antibodies have also been generated during the last decades, mostly polyclonal antibodies for basic research and not for commercial use. Recently, mouse mono- and polyclonal anti-TK1 antibodies have been developed for potential clinical purpose, i.e. for breast cancer [Zhang, *Cancer Detection Prev.*, 25:8, 2001] and lung cancer [Voeller, *Anti-Cancer Drugs*, 12:555, 2001]. One anti-TK1 monoclonal antibody is now commercial available for basic research, but not for clinical use (QED Bioscience Inc, San Diego, USA, 2003).

In the U.S. Pat. No. 5,698,409 O'Neil discloses monoclonal antibodies (mAb) generated against the enigmatically active 100 kDa tetrameric form of TK1 from Raji cells. The mAb are used for determining only this enzymatically active form of TK1 in biological samples from patients. Furthermore, O'Neil has to determine the TK activity using radiolabeled thymidine, in addition to using the mAb. The determined TK1 activities are then used for diagnosing and monitoring various forms of cancer. The properties of their anti-TK1 monoclonal antibodies raise questions about the specificity of these antibodies, i.e. they react with a protein of higher molecular weight than expected in SDS gelelectrophoresis Western blot (45 kDa versus 25 kDa in extracts of human HeLa cells). Furthermore, the antibodies detect a protein in the serum occurring in another (higher) concentration range than found by other workers in the field, i.e. they need to dilute serum 16,000 times while others use undiluted serum. These facts suggest that their antibodies react with other proteins in addition to enzymatically active TK1 and/or TK2. In addition, the method of O'Neil is impaired with the similar problems as with usage of the radiolabeled thymidine analogue discussed above.

Kuroiwa, et al, [Kuriowa, *J. Immuno. Methods*, 253:1, 2001] have developed and tested 26 anti-TK1 monoclonal antibodies. The properties of these antibodies are more as expected, i.e. they react with a protein with a molecular weight of 25 kDa in extracts of human HeLa in Western blot with no reported cross-reactivity to other proteins. When they used these antibodies in serum from patients with solid tumors using ELISA, they found no significant differences of serum TK1 levels as compared to serum TK1 levels from healthy individuals.

SUMMARY

It is a general, object of the present invention to provide a test for early prediction of progression and relapse of a cancer disease in a subject.

It is another object, of the invention to provide a decision support method for estimating the likelihood of progress of a cancer disease in a subject.

It is a particular object of the present invention to provide early prediction of local and/or metastatic appearance or recurrence of tumors in a subject following treatment of cancer.

These and other objects are met by the invention as defined by the accompanying patent claims.

Briefly, the present invention involves early prediction of, or estimation of the likelihood of, progression and relapse of a cancer disease in a subject diagnosed and possibly treated for cancer. The invention is based on determining a binding response level of an immunoreactive material (IM) comprising thymidine kinase 1 (TK1) protein in a sample, preferably a body fluid sample, e.g. blood serum sample, from a subject, preferably mammalian subject and more preferably human subject, at cancer diagnosis and/or after cancer treatment (e.g. after operation, chemotherapy, endocrine therapy radiotherapy and/or immunological therapy treatment). The likelihood of tumor recurrence is then estimated based directly on this determined IM binding response level.

The determined IM binding response level may in one embodiment be determined for the subject at multiple time occasions. Preferably, a first taking of sample and binding response determination is prosecuted no later than one month after initiation of the cancer treatment, more preferably before completion of the treatment, such as before starting the cancer treatment in the subject. A second sample is preferably taken from the subject and analyzed for IM binding response level after starting the treatment, such as within the first year following the cancer treatment. More preferably, the second IM binding response level is determined in the subject between one month up to one year, such as between one month and six months, or around 3 months, after the treatment has begun or is completed. In either case, the second IM binding response level is preferably not determined until at least one week, e.g. some weeks, one month, or multiple months, have elapsed since the determination of the first IM binding response level in the same subject.

The prediction of progress of the cancer disease is then based on a comparison of the two IM binding response levels or by investigation of a quantity derived therefrom. For example, the subject has a high likelihood of tumor relapse if the second IM binding response level is equal to or exceeds the first IM binding response level, or expressed in another way, the likelihood of tumor relapse is high if the ratio of the second (subsequent) IM binding response level and the first IM binding response level exceeds, or is equal to, one.

Alternatively, the determined IM binding response level in the subject could compared to a normal IM binding response level, as determined from body fluid samples of healthy subjects, whereby local and/or metastatic tumor appearance is predicted based on this comparison.

The IM binding response level is preferably determined by contacting the body fluid (e.g. serum) sample with a ligand that has affinity for the TO protein. In a preferred embodiment of the invention the ligand is an antibody that binds specifically to a surface exposed epitope of the TK1 protein, preferably to a defined immunogenic sequence of the C-terminal part of TK1 protein. This ligand should preferably be able to detect both enzymatically active and inactive forms of the TK1 protein and possible also the TK1 protein complexed with other macromolecules. The amount of antibody binding is then measured by a suitable and sensitive assay method, preferably the enhanced chemoluminescence (ECL) dot blot assay system and more preferably such an ECL dot blot assay system using nitrocellulose membranes.

From this measured IM binding response level a concentration of IM can be determined using a standard, e.g. recombinant human TK1 (rhTK1). In such a case, the binding response using an anti-TK1 antibody is measured in samples with different known concentrations of rhTK1 and a standard curve of binding response vs. concentration may be generated. A subsequent IM binding response level measurement from a subject treated for cancer can then be related to a corresponding IM concentration, using the standard curve. The estimation of the likelihood of cancer progression and recurrence is then based directly on this IM concentration.

This means that in the present invention, the relapse of a cancer disease in a subject treated for the disease is determined based on the binding response level or concentration level of the TK1 protein comprising immunoreactive material. This is in clear contrast to the prior art techniques that use the thymidine kinase activity for tumor recurrence prediction.

By determining the IM binding response level in a patient within, the first few months after cancer diagnosis and treatment, it is possible to detect and identify those patients that run a high risk of a subsequent (within 1 to 3 years, possibly up to 10 years, after the treatment) cancer disease relapse. Thus, the invention allows early detection of those patients, that have a high and low risks of tumor relapse, which enables differential treatments and increases the chances of success of the treatment and may prolong survival of the patient, but also avoids inefficient and thus unnecessary treatments.

The TK1 protein comprising immunoreactive material includes the TK1 protein, e.g. serum TK1 protein, an enzymatically active and/or inactive monomeric and/or polymeric (e.g. dimeric, tetrameric) form of the TK1 protein and/or the TK1 protein completed with other molecules, e.g. proteins, such as inhibitors.

The invention may be applicable to most types of cancers and is especially adapted for cancers with solid tumors, such as breast cancer, gastric cancer and lung cancer.

The invention offers the following advantages:
Early detection of treated cancer patients running a risk of tumor relapses;
Provides decision support allowing differential cancer treatment, avoiding over-treatment, and/or change of treatment strategy; and
Enables increased survival chances and quality of life of cancer patients.

Other advantages offered by the present invention will be appreciated upon reading of the below description, of the embodiments of the invention.

SHORT DESCRIPTION OF THE DRAWINGS

Figure 2:
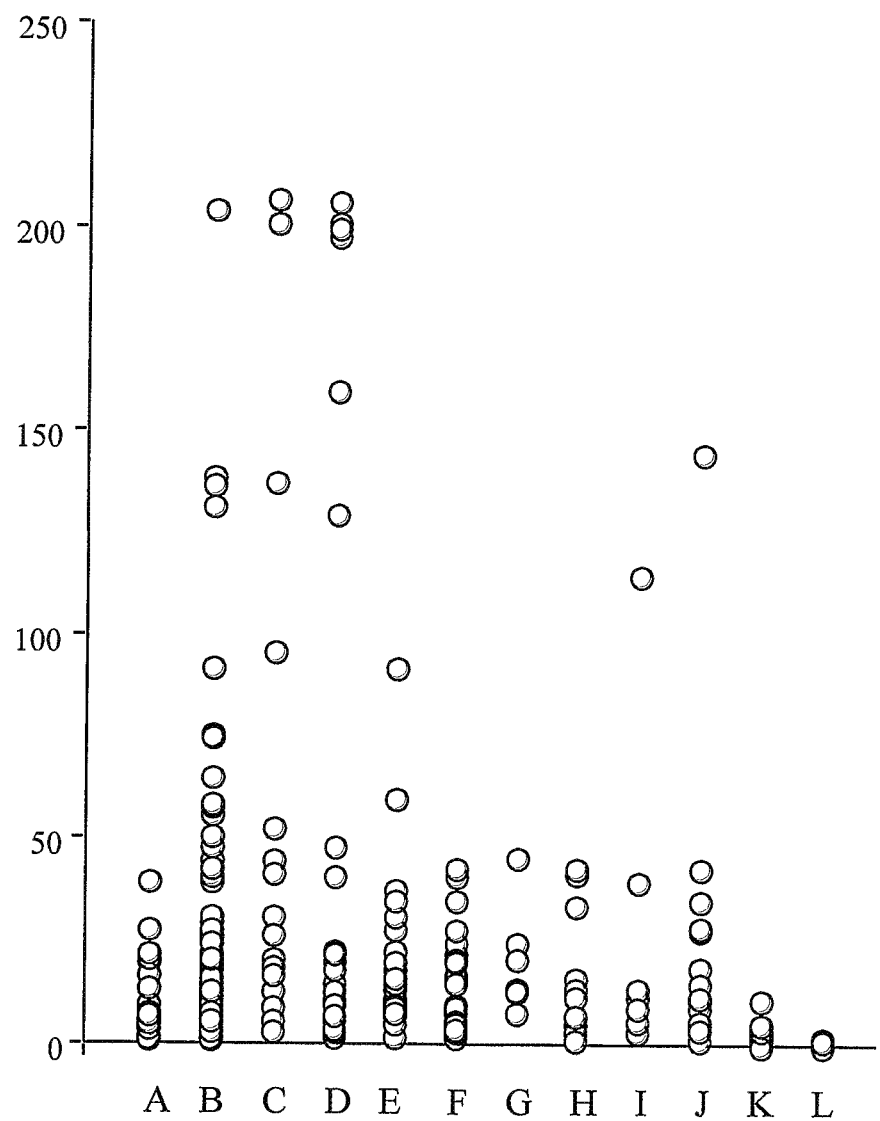
Figure 3:
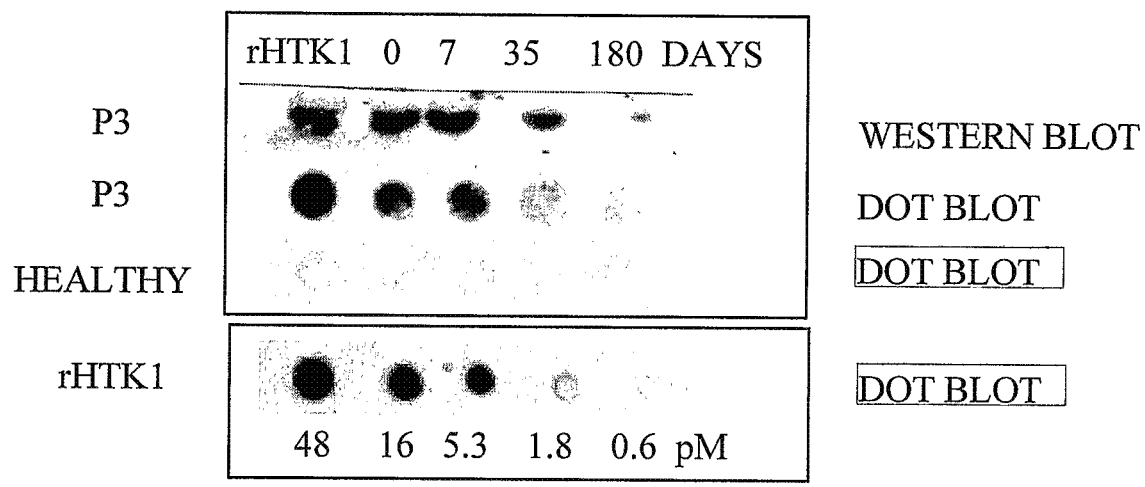
Figure 4:
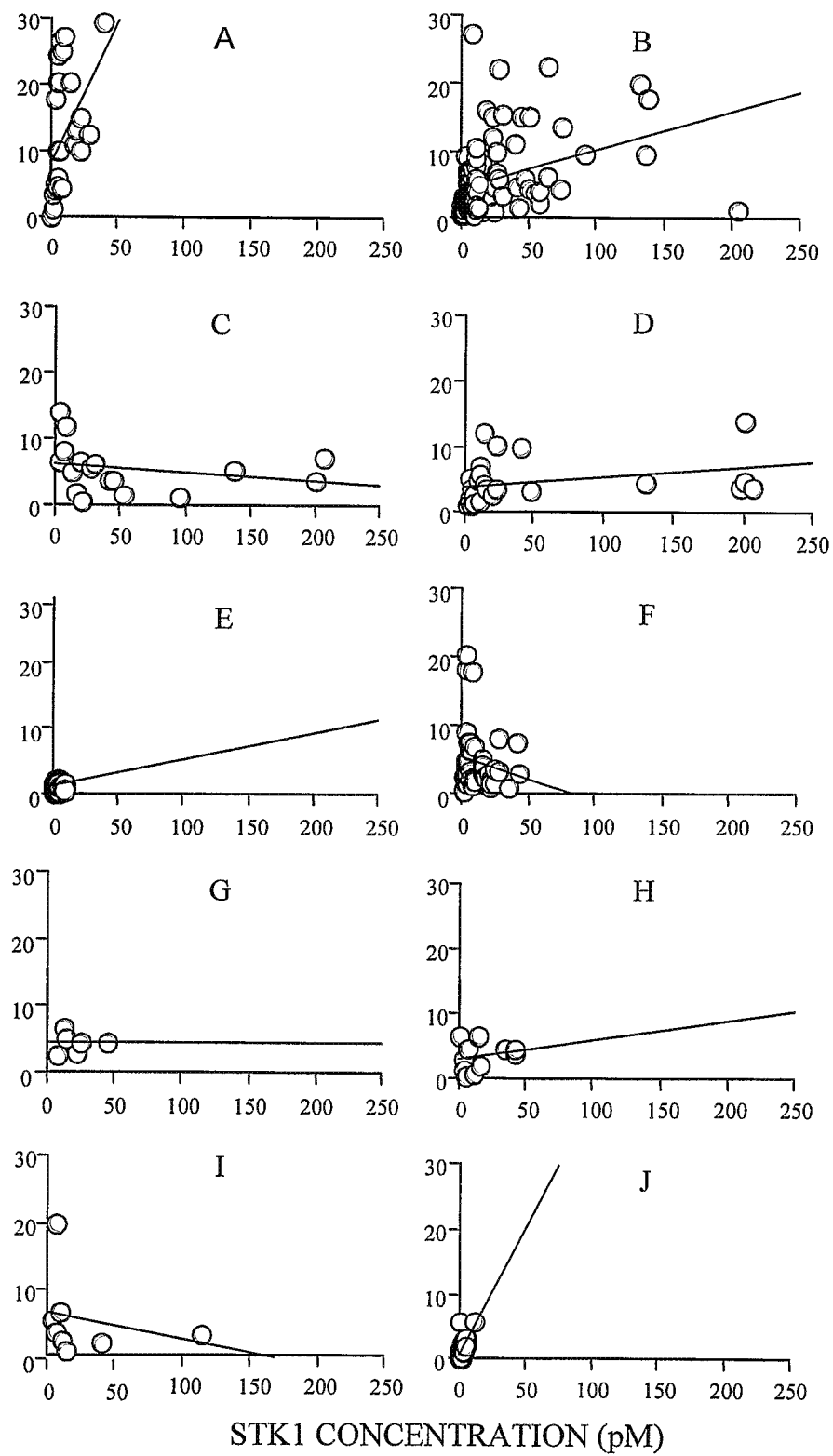
Figure 5:
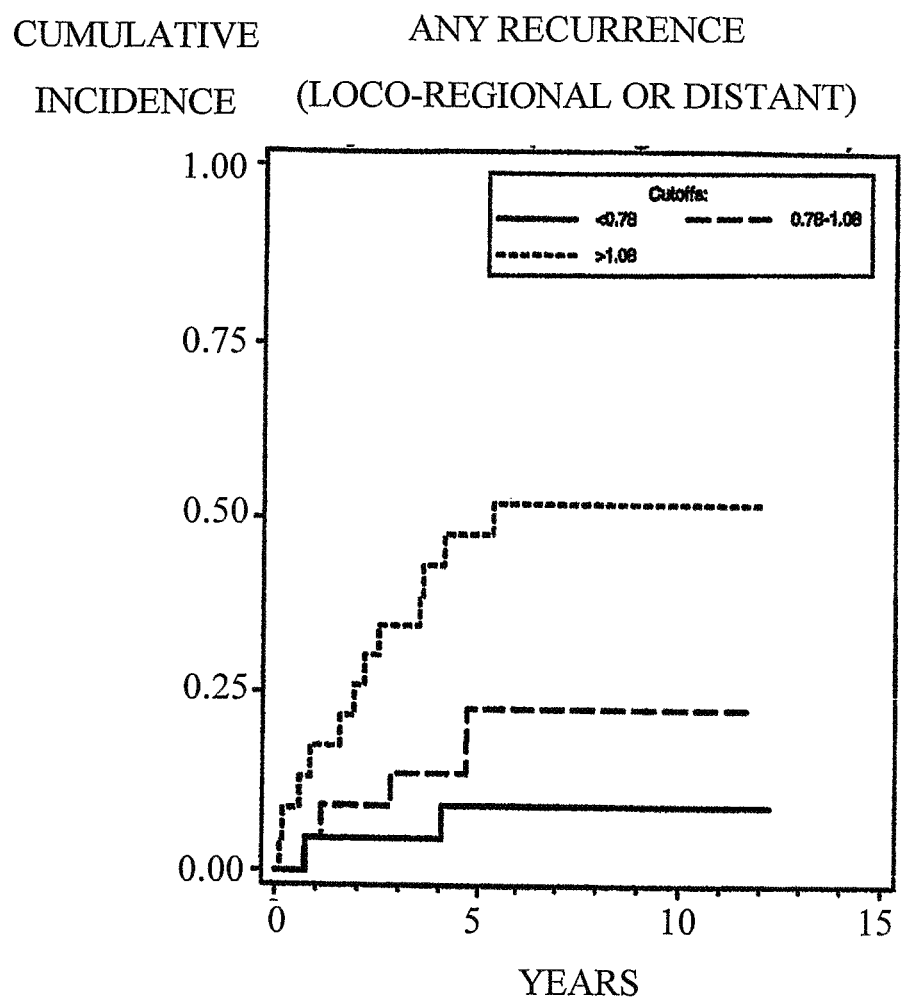
Figure 6:
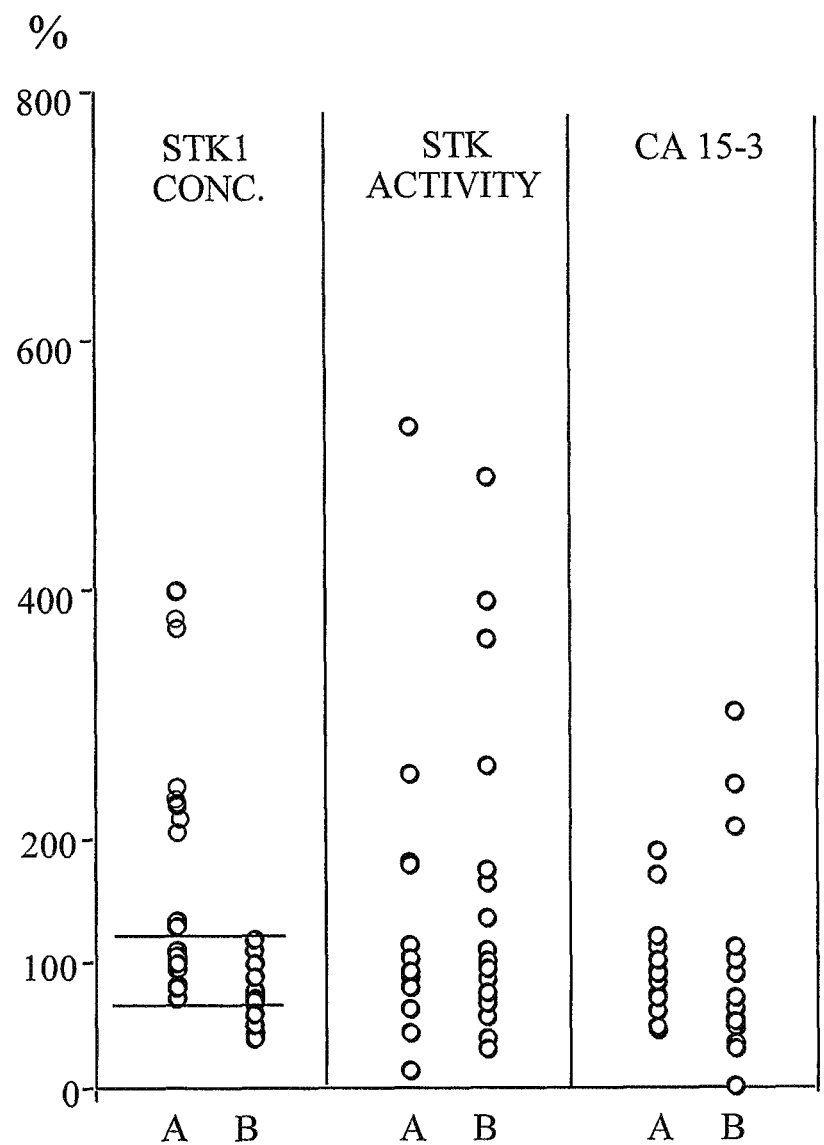
Figure 7:
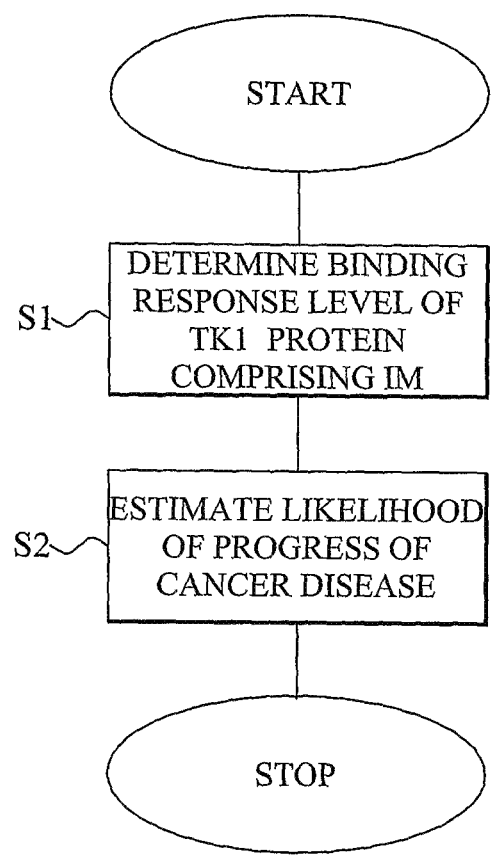

The invention together with further objects and advantages thereof, may best be understood by making reference to the following description taken together with the accompanying drawings, in which:

FIG. 1 illustrates correlation between enzyme activity of serum thymidine kinase (STK) and concentration of TK1 protein comprising immunoreactive material (IM) (STK1) in healthy individuals;

FIG. 2 illustrates IM concentration (STK1) in serum of healthy individuals and human patients with different types of tumors, where A represents leukemias, B represents gastric tumors, C represents colon tumors, D represents rectum tumors, E represents breast tumors, F represents lung tumors, G represents lymphomas, H represents hepatomas, I represents brain tumors, J represents other types of malignant tumors, K represents morphological benign lesions and L represents healthy persons;

FIG. 3 illustrates IM concentration (STK1) measured by Western blot and dot blot from a patient with a gastric cancer (P3), a dot blot of a healthy individual and of human recombinant TK1;

FIG. 4 illustrates correlation between IM concentration (STK1) and enzyme activity of STK in patients with benign lesions and malignant tumors before cancer treatment, where A represents leukemias, B represents gastric tumors, C represents colon tumors, D represents rectum tumors, E represents lung tumors, F represents lymphomas, G represents hepatomas, H represents brain, I represents morphological benign lesions tumors and J represents breast tumors;

FIG. 5 illustrates the cumulative incidence of any recurrence in 67 breast cancer patients, divided into three equal groups representing relative STK1 concentrations of <0.78, 0.78-1.08 and >1.08, as defined by the STK1 concentration determined at three months after surgery divided by the corresponding STK1 concentration at 21 days after surgery;

FIG. 6 is a comparison of IM concentration (STK1), enzyme activity of STK and concentration, of CA 15-3 in serum at 3 months after operation in 37 breast cancer patients with (A) and without (B) subsequent cancer tumor relapse expressed in percentage of measured values 21 days after operation; and FIG. 7 is an illustration of a How diagram of the tumor relapse predicting method of the present invention.

DETAILED DESCRIPTION

Unless defined otherwise, all technical and scientific terms used herein have the meaning commonly understood by a person skilled in the art to which the present invention belongs. For clarity of the invention, the following definition is used herein.

"Thymidine kinase" (ATP: thymidine-5' phosphotransferase, EC.2.7.1.21 in the International Union of Biochemistry classification system) is an enzyme of the pyrimidine salvage pathway and catalyses the phosphorylation of thymidine to thymidine monophosphate. In human cells, TK appears in two forms, a cytoplasmic thymidine kinase 1 (TK1) and a mitochondrial thymidine kinase 2 (TK2) form, encoded by different genes. "Enzyme activity of TK" refers to the roll of TK in catalyzing the phosphorylation of thymidine to thymidine monophosphate.

"TK1 protein comprising immunoreactive material (IM)" refers to a materiel or composition comprising the TK1 protein. The IM material could comprise both enzymatically active and inactive forms of the TK1 protein, including e.g. monomeric, polymeric (e.g. dimeric, tetrameric) TK1 protein forms and/or all forms of the TK1 protein. The material can also or instead include the (enzymatically active or inactive) TK1 protein completed with other molecules, including proteins and polypeptides, such as inhibitors and/or activators.

According to an aspect of the present invention there is provided a method of early prediction of progression and relapse or recurrence of a cancer disease in a subject, preferably a mammalian subject and more preferably a human subject, treated for cancer. The method comprises determination of a binding response level of an immunoreactive material (IM) comprising the thymidine kinase 1 (TK1) protein in a sample from the subject. The likelihood of progress of the cancer disease, e.g. as manifested in appearance or recurrence a cancer tumor, is then estimated based directly on the determined IM binding response level.

In a particular aspect of the invention the binding response level is determined in an immunoreactive material, that includes both enzymatically active and inactive forms of the TK1 protein. In an embodiment of the invention, this binding response level is expressed as a concentration level of IM in a sample from a subject using a ligand that has affinity for TK1. The likelihood of progression and relapse of the cancer is then estimated based directly on the determined IM concentration level.

In an embodiment of the invention the IM binding response level is determined for the subject at multiple, i.e. at least two, time occasions. The likelihood of disease relapse is then based on a comparison of these at least two binding response levels. In a preferred embodiment of the invention, the first taking of sample and binding response determination is prosecuted no later than one month after initiation of the cancer treatment, more preferably before completion of the treatment, such as before starting the cancer treatment in the subject or in connection of diagnosis of the cancer disease. The at least second sample is preferably taken from the subject and analyzed for IM binding response level alter starting the treatment, such as within the first year following the cancer treatment. More preferably, the second IM binding response level is determined in the subject between one month up to one year, such as between one month and six months, or around 3 months, after the treatment has begun or is completed. In either case, the second IM binding response level is preferably not determined until at least one week, e.g. some weeks, one month, or multiple months, has elapsed since the determination of the first IM binding response level in the same subject.

The prediction of progress of the cancer disease and/or tumor recurrence is then based on a comparison of the two IM binding response levels or by investigation of c quantity derived therefrom. For example, the subject has a high likelihood of cancer relapse if the second IM binding response level is equal to or exceeds the first IM binding response level, or expressed in another way, the likelihood of tumor relapse is high if the ratio of the second (subsequent) IM binding response level and the first IM binding response level exceeds, or is equal to, one.

The IM binding response level in the subject is preferably periodically or intermittently determined at several time occasions during and after the cancer treatment, e.g. after operation, after start, of chemotherapy treatment, after start of endocrine therapy treatment, after start of radiotherapy treatment and/or alter start of immunological therapy treatment, in the patient. Thus, the IM level is preferably determined during the first next years, e.g. up to the next 5 to 10 years, following treatment to, as early as possible, detect progress of the cancer disease in the subject. However, for most cancer types, and especially solid tumor cancer types, the method of the invention is probably able to detect any subsequent cancer relapse within the first 6 months, such as within the first 3 months, following the cancer treatment. These subsequent binding response levels are preferably compared to corresponding binding response levels determined earlier for the same subject, e.g. the first IM binding response level discussed above.

In other words, the present, invention is able to predict within the first few months (typically 0-6 months, for some cancers 0-3 months) following cancer treatment whether a subject will anew get (local and/or metastatic) tumors hack. Thus, although a cancer disease will reappear first within a couple of years after the treatment, the invention may predict its progression and relapse within a few months alter the treatment. By means of such an early prediction, additional treatment and/or change of treatment strategy may be applied in order to prevent the predicted local and/or metastatic tumor appearance. In addition, those subjects that are predicted to be likely to get a relapse may be under close surveillance to, as early as possible, detect any new tumors, and thus increase the survival chances of the subject. Identification of low risk patients with the same assay would also improve the qualitative of patients' life by reducing the risk of over-treatment or unnecessary treatments.

In another embodiment of the invention, the determined IM binding response level is compared to a normal binding response level, as determined from healthy tumor-free subjects. The estimation of the likelihood of cancer progression and relapse is then based on this comparison. For example, the disease is likely to progress and relapse if the determined IM level is significant higher than the normal IM level. As was noted above, the IM binding response level is preferably determined at multiple different time occasions, starting e.g. from before the cancer treatment and continuing during and after the treatment.

The normal or healthy subject IM binding response level (concentration or amount) to be compared with the measured IM level can be determined by measuring the IM binding response level in a series of samples, preferably body fluid samples, e.g. blood serum samples, from healthy subjects. These healthy subjects preferably do not have or have had any demonstrable tumors, i.e. exhibit no clinical sign of tumor or cancer disease. The IM binding response level of these healthy control subjects may be determined using the same methods as for the determination of the binding response level in the subject under investigation, as is discussed in more detail below. In an embodiment, the normal IM binding response level is the average of the IM binding response levels measured from the series of healthy subject samples.

The IM concentration level in healthy human subjects is about 1 pM or less, whereas for human tumor patients the level increases to several, hundred pM. A determined IM concentration level of 2 or 3 pM or above could be determined as an abnormal level, and thus may correspond to estimating a likelihood of tumor disease progression. However, the concentration level that corresponds to a likelihood of cancer disease relapse may be different for different types of tumors and different kinds of subjects.

Prior art prediction methods, as exemplified by the U.S. Pat. No. 5,698,409, are, as was briefly mentioned in the background section, based on measurement of the enzyme activity of TK (and TK1) in serum samples. In the above-identified patent, O'Neil uses monoclonal antibodies that binds to the enzymatically active tetrameric 100 kDa form of TK1, probably to the active site of the tetrameric 100 kDa form of TK1, and inhibits the TK1 enzyme activity, in order to predict recurrence of a tumor based on the TK enzyme activity O'Neil presumes that there is a direct correlation between the f serum) TK enzyme activity and the level (concentration) of TK1 comprising immunoreactive material. As is shown by the present invention, such a correlation, exists for healthy human individuals, for patients with certain non-cancer diseases, e.g. kidney malfunction, hemorrhage and lung infection. A correlation between TK serum activity and concentration can also be found for a few cancer type before the cancer treatment. However, no such a correlation has been found during or, in particular, after cancer treatment. A possible explanation for this lack of correlation between concentration of serum TK1 (STK1) and the enzyme activity of serum TK (STK) in cancer patients could be that the concentration of STK1 and the activity of STK reflect different subpopulations of thymidine kinase. In addition, there may be regulating factor(s) in serum controlling the concentration of IM/STK1 and/or activity of STK. Furthermore, the TK enzyme activity is also known to be very sensitive to changes in pH and temperature.

Thus, those prior art methods that determines likelihood of tumor recurrence based on measurement of STK enzyme activity (i.e. based on a measure in an enzyme activity domain) after cancer treatment, e.g. by using, the monoclonal antibodies disclosed in the U.S. Pat. No. 5,698,409, and the presumption of a correlation between binding response (concentration) level of STK1 and STK enzyme activity give incorrect predictions, particular in cases of solid tumors.

However, by determining the binding response level or concentration of IM (STK1) using the antibodies discussed in this invention and estimating progress of the cancer disease based directly on the measured binding response level or concentration (i.e. a measure in the binding response or concentration domain), a much more accurate tumor disease prediction is obtained.

The prediction of cancer progression according to the present invention is based on the binding response (concentration or amount) level of IM, such as concentration of the TK1 protein, in a biological sample, preferably a body fluid sample, e.g. blood serum sample, from a subject. The binding response level of IM in the (serum) sample can be determined in several different ways known to the person skilled in she art using different ligands. In a presently preferred embodiment of the invention, the IM binding response level is determined by contacting the sample with special TK antibodies and then measuring the antibody binding. This antibody binding can be measured by several methods known in the art. The IM binding response level is then preferably related to a chemically defined standard. In a presently preferred embodiment the standard is human TK1, e.g. recombinant, isolated and substantially purified human TK1 (rhTK1), which may prepared as described by Wang et al. [Wang, Biochemistry, 38:16993, 1999]. Thus, the same anti-TK antibody (ligand) that is used in the sample from a subject to be treated for or already treated for cancer is used in test samples comprising different known concentrations of rhTK1. By determining the antibody binding in respective test sample a standard curve of the correlation between antibody binding and concentration level is obtained. The IM concentration can then be determined from the measured antibody binding and the standard curve. An alternative relation between the concentration level and binding response level could be a mapping function that uses a determined IM binding response measure as input and outputs a corresponding concentration value. Such a function can be determined using the standard curve and/or the rhTK1-including test samples.

The assay method used for antibody binding has to be sensitive enough to detect the low amount of IM in subjects, especially in healthy subjects. The assay method is preferably sensitive enough to detect IM concentration levels of at least 1 pM, preferably at least. 0.7 pM, more preferably at least 0.5 pM, such as at least 0.3 pM. An example of such a sensitive assay method is enhanced chemoluminescence (ECL) dot blot assay. As is known in the art, the procedure of ECL dot blot assay is substantially the same as for Western blotting. Basically, blood serum (or another body fluid) is applied onto a membrane e.g. it nitrocellulose membrane. After (optional) blocking, primary (anti-TK1) antibodies are added, followed by biotinylated secondary antibodies. The membrane is then immersed in a buffer solution with $H_2O_2$ followed by incubation with a buffer solution with avidin-HRP-streptavidin (avidin-Horse Radish Peroxidase-streptavidin) and/or streptavidin-HRP. The Light is then detected by e.g. a digital CCD (Charged Coupled Device) camera or exposed to X-ray film. The ECL dot blot assay is able to detect concentration levels of less than 0.3 pM [He, Internal. J. Biol. Marker 15:139, 2000].

Another possible assay method is RIA (Radio Immune Assay), where (anti-TK1) antibodies are labeled with an isotope, e.g. $^{125}I$. Although this method is as sensitive as ECL dot blot, the used $^{125}I$ is an unstable isotope with a half life of a few weeks. In addition expensive detection equipment (γ-scintillation counter) is usually required for determination of antibody binding.

The antibodies used in the above-discussed IM assay method could be polyclonal and/or monoclonal antibodies that bind specifically to an epitope of the TK1 protein, preferably TK1 protein from human subjects and more preferably both enzymatically active and inactive forms of the human TK1 protein. The epitope is preferably (physically) separated from the active site of TK1, i.e. the antibodies should, not substantially affect or inhibit the enzyme activity of TK1 by direct binding to the active site. According to the invention, the antibodies preferably bind specifically to the C-terminal portion of TK1 protein and more preferably to the sequence of TK1 protein from amino acid 179 to amino acid 234, or a portion thereof, e.g. a sequence from amino acid 195 to amino acid 225, such as a sequence from amino acid 210 to amino acid 224, or a polypeptide sequence comprising the amino acid sequence of TK1 protein from amino acid 179 to amino acid 234. Examples of such antibodies are described in the U.S. Pat. No. 6,083, 707, the teaching of which is hereby incorporated by reference in the present invention. In this US Patent, polyclonal antibodies against a 1.5 amino acids (KPGEAVAARKL-FAPQ, SEQ ID NO: 1 or Acetyl-KPGEAVAARKLFAPQ, SEQ ID NO: 2) long sequence of the C terminal end of TK1 are produced. The antibodies of the invention are, thus, generated to surface exposed parts (epitopes) of TK1 protein. By using an antibody against one of the sequence discussed above, the binding response level and concentration level of TK1 protein and possibly TK1 complexed with other molecules could be determined. This means that the antibodies of the invention preferably determines a total amount of the TK1 protein, including enzymatically active and inactive forms of the TK1 protein and the TK1 protein complexed to other molecules, which include the epitopes that the antibodies have affinity for.

Blocking agents in certain sera might prevent binding of the antibodies to TK1 protein by, for example, blocking the epitope to which the antibody binds and/or changing, upon binding TK1 protein, so that the antibody binding epitope is moved from an accessible (surface) location to a location where it is inaccessible for the antibody.

In a particular embodiment, the prediction method of the invention is a decision support method, i.e. a non-diagnostic method. This means that the decision support method, will result in decision support informatics e.g. as exemplified by a binding response, concentration or likelihood value, which is merely interim results. Additional data, and the competence of a physician are typically required for providing a final diagnosis. Furthermore, other parameters than the IM binding response level (IM concentration level) may influence the progression of a tumor disease, such as the case history, age and sex of the subject, the type of tumor, genetic factors etc. Thus, the invention gives a decision support upon which a physician can base his decision, about which measures that should be taken.

The present invention is applicable on several different types of cancers, including, but not limited to, human sarcomas and carcinomas, e.g. fibrosarcoma, myxosarcoma, liposarcoma, chondrosarcoma, osteogenic sarcoma, chordoma, angiosarcoma, enotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, hemangioblastoma, oligodendroglioma, melanoma, neuroblastoma and retinoblastoma, leukemias, e.g. acute lymphocytic leukemia (ALL), and acute myelocytic leukemia (myeloblastic, promyelocytic, myelomonocytic, monocytic and erythroleukemia), chronic leukemias (chronic myelocytic leukemia, chronic granulocytic leukemia and chronic lymphocytic leukemia), polycythemia vera, lymphoma (Hodgkin's disease and non-Hodgkin's disease), multiple myeloma, Waldenström's macroglobulinemia and heavy chain disease. The present invention is in particular applicable in prediction progress of cancers with solid tumor, e.g. breast and gastric cancer.

The tumor monitoring and prediction method of the invention is summarized in FIG. 7. Starting with step S1, a binding response level of an immunoreactive material (IM) comprising (enzymatically active and inactive) TK1 protein is determined in a sample, preferably body fluid sample, e.g. blood serum sample, from a subject, preferably mammalian subject and more preferably human subject, treated for cancer. Note that the cancer treatment does not have to be completed when the taking of sample from the subject is performed. The IM binding response level is determined using an ligand, preferably an antibody that binds specifically to the TK1 protein, more preferably an antibody that hinds specifically to the C-terminal portion of TK1 protein. In step S2, the estimation, of the likelihood, of progress or relapse of the cancer disease, e.g. as manifest by local and/or metastatic tumor recurrence or appearance, is performed based directly on the determined IM binding response level. This likelihood may be estimated based on a comparison of the determined IM binding response level with an IM binding response level as determined earlier for the subject or from healthy subjects.

According to another aspect of the invention there is provided a system for predicting progression of a cancer disease in a subject treated for cancer. An IM binding response level, or concentration level of IM, e.g. concentration of serum TK1 protein, is determined in the subject, e.g. by one of the assay methods discussed in the foregoing. The determined binding response level or concentration is then the input data in the system, preferably together with a IM binding response (concentration) level, of healthy individuals and/or an earlier determined binding response level for the subject. In order to obtain an estimation of the likelihood of cancer relapse in the subject.

The system could be a computer system with dedicated software adapted for tumor progression prediction or a neural network. Several measurements of IM level from subjects treated for cancer and obtaining subsequent tumor progression and relapse and not obtaining tumor relapse, respectively, and (normal) IM binding response level from healthy subjects may be used for designing such a software. Based directly on these measurements, the software could be able to provide an estimation of tumor progression and relapse from IM binding response levels.

The system could also require additional input parameters for a more accurate estimation, such as additional case history parameters, age and sex of the subject cancer type, genetic markers, other biochemical parameters, etc. The system or dedicated software of the system could be configured for using an equation of formula with IM binding response level or IM concentration (and possible other parameters) as input in the equation. The software/system then calculates the likelihood estimation. Alternatively, one or several cutoff limits could be employed for determination of the estimation. Thus, estimating the likelihood of tumor recurrence based directly on a determined IM binding response or concentration value from a subject also anticipates that the determined IM binding response values (concentrations) are input in some (basic) function, possible with other input parameters. The basic idea is that the estimation is based directly on measures of a binding response (concentration) domain and does not require a mapping from this binding response domain to an enzyme activity domain for performing the estimation.

The system could also incorporate equipment for determination of the IM binding response level in a subjects sample, in such a case, a body fluid sample is input in the system, which determines the IM level and calculates the tumor progression and relapse likelihood estimation directly based on the IM level. Such a binding response determining equipment could be based on one of the assay methods, i.e. ECL dot Mot or RIA with anti-TK1 antibodies, discussed in the foregoing.

EXAMPLES

ECL Dot Blot Assay

The procedure of the ECL dot blot assay is the same as for Western blotting, with slight modification [He, Internal. J. Biol. Marker, 15:139, 2000]. Three µl of serum of venous blood from non-heparinised blood tubes was directly applied onto a nitrocellulose membrane (Hyband™-C, Amersham). The blood samples were taken in the morning between 7-9 AM of persons who did not take any breakfast. The drawn venous blood in the non-heparinised tubes can be stored for at least 24 hours at +4° C., or centrifuged at 1,500 g for 5 min and then stored at −20° C. for 5 years and at −80° C. for more than 10 years. Recombinant human TK1 (rhTK1) was used as a standard, as initially described by He, et al. [He, Europ. J. Cell Bio. 70:117, 1996] and modified as described by Wang, et al. [Wang, Biochemistry, 38:16993, 1999]. The employed membrane was blocked in TBS (Tris-Buffered Saline) buffer with 10% non-fat milk for 4 hours and then primary (anti-TK1) antibody was added and incubated at +4° C. over night or at room temperature for two hours. After incubation with a biotinylated secondary antibody for one hour at room temperature, the membrane was immersed in TBS buffer with 3% $H_2O_2$ for 5 min. The membrane was then incubated in TBS buffer with avidin-HRP-streptavidin and exposed to X-ray film. The intensity of a single spot on the film was determined by a Laser Densitometer. From the intensity of the rhTK1 of known concentrations, the intensity of the IM was recalculated and expressed as pM.

Characterization of Anti-TK1 Antibodies

Anti-TK1 antibodies were characterized by Western blot, isoelectric focusing, immunoprecipitation and immunohistochemistry. The results are summarized in Table 1 below. According to the Western blots, the monoclonal antibodies against the 15 amino acids long peptide sequence (SEQ ID NO: 2) (mAb1D11 and mAb1E3) or rhTK1 (mAb263 and mAb26-5) recognize the native form of the TK1 protein in human tumor cells, as well as the TK1 protein in serum of patients with malignancies, but not the denatured 25 subunit of TK1 protein. No band in the electrophorese gel was found in the TK1 negative cells, in serum of healthy persons or in the presence of competing antigen. Immunoprecipitation tests indicated that maAb1E3, although not directed to the active site of the TK1 protein, affects the enzyme activity of TK1. mAb26-3+5 and mAb1D11 inhibit TK1 activity in the supernatant by making an immunocomplex will the TK1 protein, which is collected in the pellet. Isoelectric focusing showed that the TK1 protein has a pI value of ≈7.0, when blotted with mAb26-3+5. However, no band was detected, when blotted with mAb1D11 and mAb1E3. The polyclonal rabbit anti-TK1 antibody (pAb; recognizes the sub-unit 25 kDa in SDS gelelectrophorese and gives a pI value of TK1 of ≈8.3. The chicken IgY anti-TK1 antibody (SSTK Biotech Inc., China), directed against a 31 amino acids sequence or amino acids 194 to 225 of the TK1 protein, recognize both the native form of TK1 and the subunit 25 kDa and give a pI value of ≈8.3. Finally, monoclonal antibodies (mAb USA) against the whole TK1 protein (QED Bioscience Inc, San Diego, USA) recognize the 25 kDa subunit of TK1.

The IM concentration and STK activity were also determined in patients with non-cancer diseases. In six of 19 such patients with kidney malfunction, hemorrhage, cirrhosis of liver and lung infection and non-infection diseases, IM concentration and STK activity were elevated, by 1.6 and 1.8 times, respectively, as compared to the healthy controls. In one case of hemorrhage and one case of liver cirrhosis, the IM concentration was 5 times higher and the STK activity 2-4 times above the cut-off values of 2 pM and 2.4 U/L, respectively. There was a significant correlation between the IM (STK1) concentration and the STK activity in patients with these types of non-cancer diseases (Table 2).

In Table 2, correlation and its significance values are based an Pearson's correlation coefficients.

TABLE 2

| Tumor type | STK1 concentration versus STK activity | | |
|---|---|---|---|
| | n | $r_p$ | p |
| Healthy | 43 | 0.67 | <0.01 |
| Non-cancer diseases | 19 | 0.72 | <0.01 |

TABLE 1

| Ab | Antigen | Western blot of TK1 in CEM cell lysates | | | TK1 activity | | Immuno. staining | TK1 in serum Native gel, | Comments |
|---|---|---|---|---|---|---|---|---|---|
| | | SDS gel 25 kDa TK1 | Native gel Rm 0.16 TK1 | IEF gel pI TK1 | In pellet TK1 | In sup. TK1 | Cytoplas. TK1 | | |
| CEM cells | | + − | + − | + − | + − | + − | + − | cancer patient | |
| mAb26-3 | rhTK1 | − − | + − | 7.0 − | + − | − − | + − | 7.0 | Some cross-reactions in |
| mAb26-5 | rhTK1 | − − | + − | 7.0 − | + − | − − | + − | 7.0 | malignant and normal tissue |
| mAb26-3 + 5 | rhTK1 | − − | ++ − | 7.0 − | ++ − | − − | + − | Rm 0.31 | Can be used for STK1 |
| mAb USA | TK1 | + − | | | | | + − | | Can be used for STK1, some cross-reactions in healthy serum |
| mAb1D11 | 15 aa | − − | ++ − | − − | ++ − | − − | + − | Rm 0.31 | Some cross-reactions, can be |
| mAb1E3 | 15 aa | − − | + − | − − | − − | − − | + − | Rm 0.31 | used for STK1 after purification |
| pAb | 15 aa | + − | + − | 8.3 − | ++ − | − − | ++ − | 7.0 | Weak cross-reactions |
| Chicken lgY | 31 aa | + − | + − | 8.3 | | | + − | | Good for STK1 |

All the antibodies discussed above and presented in Table 1 can be used for immunocytochemical staining, both in cell lines and in paraffin embedded material. The anti-TK1 antibody reaction was localized to the cytoplasm of tumor cells. No or very little staining in mutant cells lacking TK1 enzyme activity was found, as well as in resting lymphocytes. Thus, the anti-TK1 antibodies tested can be used to determine the IM binding response level and concentration. These antibodies also recognize different epitopes on the TK1 protein, probably identifying various subpopulations of TK1.

IM Concentration and STK Enzyme Activity in Healthy Subjects

IM (STK1) concentration as measured by the above-discussed dot blot ECL immunoassay was compared to STK enzyme activity as determined by the RIA assay in healthy persons and the results are presented in FIG. 1 and Table 2. Both the IM concentration and the STK enzyme activity were low (less then 2 pM and 2 U/L, respectively). There was a significant correlation between IM concentration and STK enzyme activity (r=0.67, p<0.01) for these healthy persons.

TABLE 2-continued

| Tumor type | STK1 concentration versus STK activity | | |
|---|---|---|---|
| | n | $r_p$ | p |
| Benign tumor | 34 | 0.63 | $0.01 < p < 0.05^a$ |
| Leukemia | 25 | 0.44 | $0.01 < p < 0.05^a$ |
| Gastric | 109 | 0.36 | <0.01 |
| Colon | 17 | −0.21 | no |
| Rectum | 28 | 0.30 | no |
| Breast | 29 | 0.58 | <0.01 |
| Lung | 39 | −0.15 | no |
| Lymphoma | 6 | 0.00 | no |
| Hepatoma | 12 | 0.26 | no |
| Brain | 8 | −0.26 | no |

$^a$Significance values are less than 0.05 but larger than 0.01.

IM Concentration and STK Activity in Tumor Patients Before Treatment

IM (STK1) concentrations from 752 tumor patients with 9 different types of malignant tumors were determined by the ECL dot blot immunoassay and was found to be increased up to 200 times, as compared to the healthy persons. IM concentrations were also measured in serum of patients with morphological benign lesions. The results of the measured concentrations are presented in FIG. 2, where A represents leukemias, B represents gastric tumors, C represents colon tumors, D represents rectum tumors, E represents breast tumors, F represents lung tumors, G represents lymphomas, H represents hepatomas, I represents brain tumors, J represents other types of malignant tumors, K represents morphological benign lesions and L represents healthy persons. In the patients with malignant tumors the concentration of IM was found from almost normal values (cut-off 2 pM) (29/752) to 100 pM (711/752), and in some cases up to 200 pM (13/752). Thus, about 95 percent of the patients with malignancy show IM concentrations above a cutoff value of IM of 2 pM.

STK enzyme activity was also determined in parallel in 264 patients with turner, benign lesions, non-cancer diseases and healthy persons. While the concentration of IM varied extensively between the various patients, STK activity showed only a limited variation. In benign lesions, leukemia, breast cancer and gastric cancer, significant correlation between IM concentration and STK activity were found for the patients before any cancer treatment (see Table 2). However, no correlation was found for the majority of the investigated tumor types in the untreated individuals, see FIG. 4.

IM (STK1) concentration was also investigated in 68 preoperative patients with cancer of the gastro-intestinal track with regard to the presence or absence of metastasis (no metastasis (M0) and metastasis (M1) n=22) and the degree of differentiation (high or moderate high differentiation n=56, and low differentiation n=12) according to guidelines set out in the clinical TNM (UICC, Fifth edition, 1997), The results are summarized in Table 3. The IM concentrations were 4.5 times higher in the patients with metastasis (M1), as compared to patients without metastasis (M0) ($p<0.01$). The concentration in the patients with low differentiated tumors, was also higher, as compared to patients with high/moderate high differentiated tumors, although not significantly different ($p>0.05$).

TABLE 3

|  | No. | IM conc. (pM) | t value | p value |
|---|---|---|---|---|
| Differentiation | 68 |  |  |  |
| High or middle | 56 | 38 ± 70 | 0.88 | >0.05 |
| Low | 12 | 57 ± 67 |  |  |
| Metastasis | 68 |  |  |  |
| Yes (M1) | 22 | 87 ± 106 | 4.20 | <0.001 |
| No (M0) | 46 | 19 ± 20 |  |  |

Gastric Cancer

IM (STK1) concentrations and STK enzyme activities were determined in 43 patients with gastric cancer (GC) by means of the dot blot ECL immunoassay and by the RIA-activity assay, respectively. FIG. 3 illustrates a Western blot and dot blot from one example of a tumor patient (P3), a dot blot of a healthy individual (healthy) and of different concentrations of human recombinant TK1 (rhTK1). The determined STK1 concentration and STK activity values of preoperative patients are presented in Table 4. The IM concentration and the STK activity were significant elevated in the tumor patients before operation.

TABLE 4

|  | IM conc. (pM) | STK activity (U/l) | 2-tailed p between GC and healthy sera | | Linear correlation coefficients between IM conc. and STK activity |
|---|---|---|---|---|---|
|  |  |  | IM | STK activity |  |
| Preoperative GC (n = 43) | 27.7 ± 26.7 | 5.9 ± 4.6 | 0.012 | 0.0003 | r = 0.36 |
| Healthy (n = 43) | 0.98 ± 0.4 | 1.1 ± 0.4 |  |  | r = 0.33 |

Thirty-five days after operation, the IM concentrations decreased significantly by about half in tumor free cases, ($p=0.0106$), while the STK enzyme activities did not. In the patients with metastasis (M1), IM concentration increased further to 173% 35 days after operation. No such increase was seen in STK enzyme activity, see Table 5. The unchanged IM concentration in M0 patients at day 7 alter operation is partly due to an increase in the IM concentration in connection with operation trauma (data not shown).

TABLE 5

|  | IM conc. (pM) | STK activity (U/I) | 2-tailed p between 0-day and 7-day or 35-day postoperative sera | | Spearmen's correlation coeff. between IM conc. and STK activity |
|---|---|---|---|---|---|
|  |  |  | IM | STK activity |  |
| 0 day |  |  |  |  |  |
| M0 (n = 8) | 18.21 ± 12.7 | 11.1 ± 3.8 |  |  | R = 0.833  p = 0.01 |
| M1 (n = 6) | 31.6 ± 29.9 | 5.0 ± 2.1 |  |  | R = 0.371  p = 0.468 |
| 7 days |  |  |  |  |  |
| M0 (n = 8) | 19.9 ± 10.3 | 12.3 ± 3.1 | 0.0751 | 0.0741 | R = 0.81  p = 0.015 |
| M1 (n = 6) | 30.7 ± 30.5 | 4.7 ± 1.9 | 0.0672 | 0.107 | R = 0.37  p = 0.968 |

TABLE 5-continued

|  | IM conc. (pM) | STK activity (U/I) | 2-tailed p between 0-day and 7-day or 35-day postoperative sera | | Spearmen's correlation coeff. between IM conc. and STK activity | |
|---|---|---|---|---|---|---|
|  |  |  | IM | STK activity |  |  |
| 35 days |  |  |  |  |  |  |
| M0 (n = 8) | 9.60 ± 9.0 | 10.2 ± 5.6 | 0.0106 | 0.797 | R = 0.61 | p = 0.072 |
| M1 (n = 6) | 54.9 ± 17.1 | 4.6 ± 2.2 | 0.0605 | 0.329 | R = 0.812 | p = 0.042 |

As is evident from Tables 4 and 5, the IM concentrations can be used to monitor the results of the treatment in gastric cancer, in contrast to STK enzyme activity. Furthermore, the IM concentration level, but not the STK activity, is able to detect relapse of the cancer disease.

Leukemias

IM (STK1) concentration as measured by the dot blot ECL immunoassay and STK enzyme activities measured by RIA assay were determined in 24 patients with leukemia. There was a significant correlation between these two parameters in the patients before start of the treatment (r=0.44), see diagram A in FIG. 4.

Of these 24 patients 6 were followed during and after treatment. There was a reduction in IM concentration in those patients receiving chemotherapy. When the chemotherapy was ended, the IM concentration increased. The STK enzyme activity was still high after the start of therapy, which indicates that the concentration of IM is a more reliable assay to predict the outcome of the treatment as compared to the STK activity.

Breast Cancer

The IM (STK1) concentrations in serum in a cohort of 120 breast cancer patients, included in a controlled clinical trial of adjuvant endocrine therapy, were determined in 67 of these patients three month after operation, using the anti-TK1 chicken IgY antibody (see Table 1). The IM concentration at three months was related to that obtained at 21 days after operation, Twelve patients developed distant metastatic cancer disease and 7 loco-regional tumors as the first event during a median follow-up time of 11.6 years.

The 67 patients were subdivided into three equally sized groups of patients with a relative IM concentrations of <0.78, 0.78-1.08 or >1.08, as determined by dividing the IM concentration at three months after surgery with the corresponding IM concentration 21 days after operation. A multivariate analysis of patients with any tumor recurrences (distant- or loco-regional), considering nodal- and ER-status, tumor size, endocrine treatment, and age, showed that the patients with a relative IM concentration>1.08 were statistical significant different from those patient who have a relative IM concentration of <0.78 (p=0.004). The hazard rate ratio for developing any recurrences in the patients with a relative IM concentration>1.08 was about 6-7 times higher than patients with the relative concentrations<0.78.

TABLE 6

| Type of 1st event | | Unadjusted effect | | Adjusted effect[a] | |
|---|---|---|---|---|---|
| IM ratio[b] | Events/ Patients | Hazard rate ratio (95% CI[d]) | P-value[c] | Hazard rate ratio (95% CI[d]) | P-value[c] |
| Distant recurrence | | | | | |
| <0.78 | 2/22 | 1 | 0.056 | 1 | 0.19 |
| 0.78-1.08 | 3/22 | 1.5 (0.3-9.0) | | 1.2 (0.2-7.3) | |
| >1.08 | 7/23 | 3.8 (0.8-18.1) | | 2.5 (0.5-12.1) | |
| Any recurrence[e] | | | | | |
| <0.78 | 2/22 | 1 | <0.001 | 1 | 0.004 |
| 0.78-1.08 | 5/22 | 2.6 (0.5-13.6) | | 2.3 (0.4-12.3) | |
| >1.08 | 12/23 | 7.7 (1.7-34.5) | | 6.1 (1.3-28.5) | |

[a]Adjusted for age (<45 years, ≥45 years), nodal status (pN0, pN+), tumor size (<20 mm, ≥20 mm), ER status (ER−, ER+) and endocrine treatment (yes, no). Seven patients are excluded from this analysis due to missing information on ER status.
[b]Ratio between IM concentration measured at 3 months and 3 weeks after operation. Cut off points were obtained by dividing the IM distribution into 3 equally sized groups.
[c]Test for trend.
[d]Confidence interval.
[e]Loco-regional or distant reccurence.

The estimated cumulative incidence rates of any recurrence at 5 years were 0.09 (95% CI: 0.02-0.34), 0.23 (95% CI: 0.11-0.49) and 0.48 (95% CI: 0.31-0.73) for the relative STK1 concentrations <0.78, 0.78-1.08 and >1.08, respectively, see FIG. 5. Thus, a high IM concentration 3 months after the cancer treatment, as represented by the group>1.08, is a clear indication of a high likelihood of (loco-regional or distant) tumor recurrence.

IM (STK1) concentration and STK enzyme activity were determined in 37 of the patients. These results were also compared with CA 15-3 determinations, which is regarded as "the golden marker" within the turner marker field. FIG. 6 illustrates the determined IM concentration. STK activity and CA 15-3 concentration at 3 months after operation expressed as percentage of corresponding values 21 days after operation. In 15 patients (A) there was a relapse of tumor within 1 to 5 years following the operation, whereas there was no tumor relapse for 22 patients (B). As is shown in the figure, already at 3 months after operation the IM concentration was markedly higher in 50-60% of those patients (A) that 1 to 5 years later again developed tumors. However, there was no difference in STK activities or CA 15-3 values in the patients with (A) or without (B) any recurrent tumors. The IM concentration also predicted 25-30% of those patients (B) who did not subsequently get recurrent tumor disease.

Thus, there is concluded that there is a significant trend toward higher relative IM concentrations in patients developing distant and/or loco-regional recurrent cancer disease, during the follow up time of 11.6 years.

Such information can be used to avoid, prolong or change adjuvant therapy due to an improved risk assessment.

It will be understood by a person, skilled in the art that various modifications and changes may be made to the present invention without departure from the scope thereof, which is defined by the appended claims.

What is claimed is:

1. A method of determining a likelihood of a future solid tumor cancer relapse in a human subject who has completed solid tumor cancer surgery, solid tumor cancer radiotherapy treatment and/or solid tumor cancer chemotherapy treatment and in whom a solid tumor cancer relapse has not been detected, wherein the solid tumor cancer is breast cancer or gastric cancer, the method comprising:
   (i) contacting an antibody that binds specifically to a serum form of thymidine kinase 1 (STK1) protein with a blood serum sample taken from the subject within one to six months after completing the surgery, the radiotherapy treatment and/or the chemotherapy treatment, and before any breast cancer or gastric cancer solid tumor cancer relapse has been detected, wherein said subject had no detectable cancer tumor when the blood serum sample was taken;
   (ii) determining an amount of antibody binding to the STK1 protein in the blood serum sample;
   (iii) correlating said amount of antibody binding to the STK1 protein to a concentration of STK1 protein in the blood serum sample using a standard curve defining a correlation between an amount of antibody binding to recombinant human TK1 (rhTK1) and a concentration of rhTK1;
   (iv) contacting said antibody with a reference blood serum sample taken from said subject before completion of said surgery, said radiotherapy treatment and/or said chemotherapy treatment of said human subject;
   (v) determining a reference amount of antibody binding to said STK1 protein in said reference blood serum sample;
   (vi) correlating said reference amount of antibody to a reference concentration of STK1 protein in the reference blood serum sample using said standard curve;
   (vii) generating decision support information comprising a higher or lower likelihood of a future cancer relapse in said subject within one to ten years after completion of said surgery, said radiotherapy treatment and/or said chemotherapy treatment, wherein
      (a) if the solid tumor cancer is breast cancer, a ratio of said concentration of said STK1 protein and said reference concentration of said STK1 protein of greater than 1.08 defines a higher likelihood of a future cancer relapse, and a ratio of said concentration of said STK1 protein and said reference concentration of said STK1 protein of less than or equal to 0.78 defines a lower likelihood of future cancer relapse, and
      (b) if the solid tumor cancer is gastric cancer, a ratio of said concentration of said STK1 protein and said reference concentration of said STK1 protein of greater than 1.98 defines a higher likelihood of a future cancer relapse and a ratio of said concentration of said STK1 protein and said reference concentration of said STK1 protein of less than or equal to 0.35 defines a lower likelihood of future cancer relapse; and
   (viii) providing notice of the decision support information to a physician monitoring said subject for solid tumor cancer relapse.

2. A method of determining a likelihood of a future solid tumor cancer relapse in a human subject who has completed solid tumor cancer surgery, solid tumor cancer radiotherapy treatment and/or solid tumor cancer chemotherapy treatment and in whom a solid tumor cancer relapse has not been detected, wherein the solid tumor cancer is breast cancer or gastric cancer, the method comprising:
   (i) contacting an antibody that binds specifically to a serum form of thymidine kinase 1 (STK1) protein with a blood serum sample taken from the subject within one to six months after completing the surgery, the radiotherapy treatment and/or the chemotherapy treatment, and before any breast cancer or gastric cancer solid tumor cancer relapse has been detected, wherein said subject had no detectable cancer tumor when the blood serum sample was taken;
   (ii) determining an amount of antibody binding to the STK1 protein in the blood serum sample;
   (iii) correlating said amount of antibody binding to the STK1 protein to a concentration of STK1 protein in the blood serum sample using a standard curve defining a correlation between an amount of antibody binding to recombinant human TK1 (rhTK1) and a concentration of rhTK1;
   (iv) contacting said antibody with a reference blood serum sample taken from said subject before completion of said surgery, said radiotherapy treatment and/or said chemotherapy treatment of said human subject;

(v) determining a reference amount of antibody binding to said STK1 protein in said reference blood serum sample;

(vi) correlating said reference amount of antibody to a reference concentration of STK1 protein in the reference blood serum sample using said standard curve;

(vii) generating decision support information comprising a higher or lower likelihood of a future cancer relapse in said subject within one to ten years after completion of said surgery, said radiotherapy treatment and/or said chemotherapy treatment, wherein (a) if the solid tumor cancer is breast cancer, a ratio of said concentration of said STK1 protein and said reference concentration of said STK1 protein of greater than 1.08 defines a higher likelihood of a future cancer relapse, and a ratio of said concentration of said STK1 protein and said reference concentration of said STK1 protein of less than or equal to 0.78 defines a lower likelihood of future cancer relapse, and (b) if the solid tumor cancer is gastric cancer, a ratio of said concentration of said STK1 protein and said reference concentration of said STK1 protein of greater than 1.98 defines a higher likelihood of a future cancer relapse and a ratio of said concentration of said STK1 protein and said reference concentration of said STK1 protein of less than or equal to 0.35 defines a lower likelihood of future cancer relapse; and (viii) providing notice of the decision support information to a physician monitoring said subject for solid tumor cancer relapse, wherein said antibody binds specifically to a C-terminal portion of said STK1 protein corresponding to a portion of a sequence from amino acid 179 to amino acid 234 in human thymidine kinase 1 EC 2.7.1.21 (SEQ ID NO: 3) in the International Union of Biochemistry classification system.

3. The method according to claim 1, wherein said antibody binds specifically to a peptide selected from SEQ ID NO: 1 and SEQ ID NO: 2.

4. The method according to claim 1, wherein determining said amount of antibody binding comprises determining said amount of antibody binding to said STK1 protein in said blood serum samples by an enhanced chemoluminescence (ECL) dot blot assay system comprising a Charge Coupled Device (CCD) camera.

5. The method according to claim 1, wherein the method further comprises selecting differential cancer treatment for the subject based on the decision support information.

* * * * *

```
                              SEQUENCE LISTING

<160> NUMBER OF SEQ ID NOS: 3

<210> SEQ ID NO 1
<211> LENGTH: 15
<212> TYPE: PRT
<213> ORGANISM: Homo sapiens
<300> PUBLICATION INFORMATION:
<302> TITLE: Thymidine kinase TK1, peptide, corresponding antibodies and
      use of these in determination of tumor proliferation
<310> PATENT DOCUMENT NUMBER: US 6,083,707
<311> PATENT FILING DATE: 1995-04-21
<313> RELEVANT RESIDUES IN SEQ ID NO: (1)..(15)

<400> SEQUENCE: 1

Lys Pro Gly Glu Ala Val Ala Ala Arg Lys Leu Phe Ala Pro Gln
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: 15 amino acids of C-terminal end of human TK1
      with an acetyl group bound to amino acid 1.
<220> FEATURE:
<221> NAME/KEY: MISC_FEATURE
<222> LOCATION: (1)..(1)
<223> OTHER INFORMATION: Acetyl-Lysine
<300> PUBLICATION INFORMATION:
<302> TITLE: Thymidine kinase TK1, peptide, corresponding antibodies and
      use of these in determination of tumor proliferation
<310> PATENT DOCUMENT NUMBER: US 6,083,707
<311> PATENT FILING DATE: 1995-04-21
<313> RELEVANT RESIDUES IN SEQ ID NO: (1)..(15)

<400> SEQUENCE: 2

Xaa Pro Gly Glu Ala Val Ala Ala Arg Lys Leu Phe Ala Pro Gln
1               5                   10                  15

<210> SEQ ID NO 3
<211> LENGTH: 234
<212> TYPE: PRT
<213> ORGANISM: Homo sapiens
<300> PUBLICATION INFORMATION:
<308> DATABASE ACCESSION NUMBER: P04183
<309> DATABASE ENTRY DATE: 2002-09-19
<313> RELEVANT RESIDUES IN SEQ ID NO: (1)..(234)

<400> SEQUENCE: 3

Met Ser Cys Ile Asn Leu Pro Thr Val Leu Pro Gly Ser Pro Ser Lys
1               5                   10                  15

Thr Arg Gly Gln Ile Gln Val Ile Leu Gly Pro Met Phe Ser Gly Lys
            20                  25                  30

Ser Thr Glu Leu Met Arg Arg Val Arg Arg Phe Gln Ile Ala Gln Tyr
        35                  40                  45

Lys Cys Leu Val Ile Lys Tyr Ala Lys Asp Thr Arg Tyr Ser Ser Ser
    50                  55                  60

Phe Cys Thr His Asp Arg Asn Thr Met Glu Ala Leu Pro Ala Cys Leu
65                  70                  75                  80

Leu Arg Asp Val Ala Gln Glu Ala Leu Gly Val Ala Val Ile Gly Ile
                85                  90                  95

Asp Glu Gly Gln Phe Phe Pro Asp Ile Val Glu Phe Cys Glu Ala Met
            100                 105                 110
```

```
Ala Asn Ala Gly Lys Thr Val Ile Val Ala Ala Leu Asp Gly Thr Phe
        115                 120             125
Gln Arg Lys Pro Phe Gly Ala Ile Leu Asn Leu Val Pro Leu Ala Glu
        130             135             140
Ser Val Val Lys Leu Thr Ala Val Cys Met Glu Cys Phe Arg Glu Ala
145             150                 155                 160
Ala Tyr Thr Lys Arg Leu Gly Thr Glu Lys Glu Val Glu Val Ile Gly
                165             170                 175
Gly Ala Asp Lys Tyr His Ser Val Cys Arg Leu Cys Tyr Phe Lys Lys
            180             185                 190
Ala Ser Gly Gln Pro Ala Gly Pro Asp Asn Lys Glu Asn Cys Pro Val
        195             200                 205
Pro Gly Lys Pro Gly Glu Ala Val Ala Ala Arg Lys Leu Phe Ala Pro
        210             215             220
Gln Gln Ile Leu Gln Cys Ser Pro Ala Asn
225             230
```